United States Patent
Bailey et al.

(10) Patent No.: US 9,975,828 B2
(45) Date of Patent: *May 22, 2018

(54) PROCESS FOR PRODUCING ETHANOL

(71) Applicant: BP P.L.C., London (GB)

(72) Inventors: Craig Bailey, Middlesex (GB); Leslie William Bolton, London (GB); Jon Michael Stewart Deeley, Middlesex (GB)

(73) Assignee: BP P.L.C., London (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/315,192

(22) PCT Filed: Jun. 18, 2015

(86) PCT No.: PCT/EP2015/063692
§ 371 (c)(1),
(2) Date: Nov. 30, 2016

(87) PCT Pub. No.: WO2015/193423
PCT Pub. Date: Dec. 23, 2015

(65) Prior Publication Data
US 2017/0190644 A1    Jul. 6, 2017

(30) Foreign Application Priority Data

Jun. 19, 2014 (EP) .................................. 14173116

(51) Int. Cl.
*C07C 29/00* (2006.01)
*C07C 29/149* (2006.01)
*C07C 67/08* (2006.01)

(52) U.S. Cl.
CPC ............ *C07C 29/149* (2013.01); *C07C 67/08* (2013.01)

(58) Field of Classification Search
CPC .............................. C07C 29/149; C07C 67/08
USPC ........................................................ 568/885
See application file for complete search history.

(56) References Cited

U.S. PATENT DOCUMENTS

2011/0004034 A1*  1/2011  Daniel ................. C07C 29/149
                                                                       568/902

FOREIGN PATENT DOCUMENTS

| EP | 0 060 719 B1 | 11/1985 |
| GB | 2 150 560 A | 7/1985 |
| WO | WO 2009/063173 A1 | 5/2009 |

* cited by examiner

*Primary Examiner* — Sikarl A Witherspoon
(74) *Attorney, Agent, or Firm* — Nixon & Vanderhye P.C.

(57) ABSTRACT

Hydrogenation of methyl acetate to methanol and ethanol by feeding a hydrogenation feed of methyl acetate, water, hydrogen and a carbon oxide into a hydrogenation unit containing a copper-zinc oxide hydrogenation catalyst to produce a hydrogenation product stream of ethanol, methanol, unreacted methyl acetate, water, unreacted hydrogen, carbon monoxide, carbon dioxide, and ethyl acetate. The hydrogenation unit is operated in the vapor phase at elevated temperature and pressure. The total molar ratio of hydrogen to methyl acetate fed to the hydrogenation unit is 5:1 to 20:1. The total molar ratio of methyl acetate to carbon oxide(s) fed to the hydrogenation unit is 1:2 to 100:1. The hydrogenation product stream is separated into a liquid stream containing ethanol, methanol, unreacted methyl acetate, water and ethyl acetate, and a gaseous stream containing unreacted hydrogen, carbon monoxide and carbon dioxide, and a portion of the gaseous stream is recycled to the hydrogenation unit.

14 Claims, No Drawings

PROCESS FOR PRODUCING ETHANOL

This application is the U.S. national phase of International Application No. PCT/EP2015/063692 filed Jun. 18, 2015 which designated the U.S. and claims priority to European Patent Application No. 14173116.6 filed Jun. 19, 2014, the entire contents of each of which are hereby incorporated by reference.

The present invention relates to process for the production of ethanol. In particular, the present invention relates to a process for the production of ethanol by the hydrogenation of methyl acetate to form ethanol and methanol.

In recent years, increased use and demand for ethanol has led to a greater interest in processes relating to the production of ethanol.

Many methods for the production of ethanol from a variety of feedstocks are known in the art. For instance, processes for the preparation of ethanol via fermentation processes, in particular by the fermentation of biomass, are well known. The term "biomass" as used herein refers to any source of organic material from biological origin. Examples of fermentation processes include the direct fermentation of biomass, such as sources of a carbohydrate, to ethanol, as well as the fermentation of derivatives of biomass to ethanol. For instance, bioethanol may be obtained by fermentation of feedstocks derived from sugar cane, such as sugar cane molasses and sugar cane juice; sugar beet, such as sugar beet molasses and sugar beet juice; cereal crops, such as corn or wheat, and cereal crop derived feedstocks, such as corn syrup; and lignocellulosic materials, such as fast growing grasses or "energy grasses". Alternative methods for the preparation of ethanol via fermentation processes include the preparation of ethanol by fermentation process performed on a feed stream comprising carbon monoxide and hydrogen, such as synthesis gas; such processes are referenced and described in WO 2012/062633 A1.

Methods for the thermochemical preparation of ethanol are also well known in the art and such methods include the direct synthesis of alcohols from synthesis gas, the preparation of alcohols by the hydrogenation of carboxylic acids and/or esters thereof, and the hydration of alkenes.

WO 2009/063173 A1 discloses a process for the production of ethanol from ethanoic acid and $H_2$, characterised by the following steps:

(1) introducing ethanoic acid, together with methanol and/or ethanol into an esterification reactor to produce methyl ethanoate and/or ethyl ethanoate, (2) introducing ethanoate from step (1), together with $H_2$ and water, into a hydrogenation unit to produce a stream comprising ethanol, unreacted ethanoate and optionally methanol, (3) separating the resulting stream, from step 2, into unreacted ethanoate and ethanol and optionally methanol, (4) optionally reintroducing ethanoate, from step 3, into the esterification reactor of step (1), (5) using at least a part of the methanol and/or the ethanol of step 3, as the methanol and/or ethanol feed of the esterification reactor of step (1), and (6) recovering ethanol, from step 3.

EP0060719B1 discloses a process for the production of methyl acetate which process comprises reacting in an esterification reaction vessel methanol at elevated temperature with acetic acid in the presence of an esterification catalyst and an entrainer which is sparingly soluble in water and which forms a minimum boiling point azeotrope therewith to form a product comprising entrainer, methyl acetate and water, and in a distillation column, recovering from the product an overhead fraction comprising methyl acetate, characterised in that from an intermediate point in the column there is removed a liquid sidestream fraction comprising water and entrainer.

There remains a need in the art to provide an improved and/or optimised process for the preparation of ethanol from methyl acetate. There also remains a need in the art to provide an improved and/or optimised process for the preparation of ethanol from acetic acid. Such improvement and/or optimisation may be obtained by one or more of the following: an increased simplification of the process; an increased integration of the steps of the process; a reduction in the amount of energy required in the process; an increased productivity of the process; an increased selectivity of the process to methanol; an increased selectivity of the process to ethanol; and, a reduction in the amount of by-products formed in the process.

The present invention provides a process for the hydrogenation of methyl acetate to methanol and ethanol comprising feeding a hydrogenation feed composition comprising methyl acetate and water, together with hydrogen and at least one carbon oxide selected from carbon monoxide and carbon dioxide, into a hydrogenation unit containing a copper-zinc oxide hydrogenation catalyst and hydrogenating the methyl acetate to produce a hydrogenation product stream comprising ethanol, methanol, unreacted methyl acetate, water, unreacted hydrogen, carbon monoxide, carbon dioxide, and ethyl acetate, wherein said hydrogenation unit is operated in the vapour phase at elevated temperature, preferably at a temperature in the range of from 180 to 270° C., and elevated pressure, preferably in the range of from 20 to 100 bara, and wherein the total molar ratio of hydrogen to methyl acetate fed to the hydrogenation unit is in the range of from 5:1 to 20:1, and the total molar ratio of methyl acetate to carbon oxide(s) fed to the hydrogenation unit is in the range of from 1:2 to 100:1, and wherein the hydrogenation product stream is separated into a first liquid product stream comprising the majority of the ethanol, methanol, unreacted methyl acetate, water, and ethyl acetate, and a first gaseous product stream comprising the majority of the unreacted hydrogen, carbon monoxide, and carbon dioxide, and wherein at least a portion of the first gaseous product stream is recycled to the hydrogenation unit.

A second aspect of the present invention provides a process for the manufacture of ethanol from acetic acid and hydrogen, wherein said process comprises the following steps:

(A) reacting acetic acid together with methanol in an esterification reaction vessel to produce a hydrogenation feed composition comprising methyl acetate and water;

(B) feeding the hydrogenation feed composition from step (A), together with hydrogen and at least one carbon oxide selected from carbon monoxide and carbon dioxide, into a hydrogenation unit and hydrogenating the methyl acetate to methanol and ethanol in accordance with the first aspect of the present invention;

(C) separating a lower boiling product stream comprising methanol, methyl acetate and ethyl acetate, and a higher boiling product stream comprising ethanol and water from the first liquid product stream produced in the process of step (B); and, optionally (D) removing water from the higher boiling product stream of step (C).

A third aspect of the present invention provides a process for the production of ethanol from acetic acid and hydrogen, said process comprising the following steps:

(1) in an esterification reaction vessel, reacting methanol with acetic acid at elevated temperature in the presence of an esterification catalyst and an entrainer, said entrainer being sparingly soluble in water and forms a minimum boiling point azeotrope therewith, to form an esterification product composition comprising entrainer, unreacted methanol, methyl acetate and water, and, in a distillation column, recovering from the esterification product composition an overhead product fraction comprising methyl acetate, methanol and water, and, from an intermediate point in the distillation column, removing a liquid sidestream fraction comprising water, methanol, entrainer and methyl acetate; wherein the molar ratio of acetic acid to methanol in the esterification reaction vessel is in the range of from 1:1.1 to 1:1.8, preferably in the range of from 1:1.2 to 1:1.6, and the distillation column is operated at a head pressure of at most 5 bara, preferably at most 3 bara, more preferably at most 2 bara, and wherein the amount of water present in the overhead product fraction comprising methyl acetate, methanol and water is in the range of from 0.1 to 10 mol %, preferably from 0.5 to 7 mol %.

(2) feeding a hydrogenation feed composition consisting of at least part of the overhead product fraction from step (1), together with hydrogen and at least one carbon oxide selected from carbon monoxide and carbon dioxide, into a hydrogenation unit and hydrogenating the methyl acetate to methanol and ethanol in accordance with the first aspect of the present invention;

(3) separating a lower boiling product stream comprising methanol, methyl acetate and ethyl acetate, and a higher boiling product stream comprising ethanol, water, from the first liquid product stream from step (2) in a distillation column operated at a head pressure of at most 5 bara, preferably at most 3 bara;

(4) recycling at least part of the lower boiling product stream from step (3), preferably at least 80 vol. % of the lower boiling product stream from step (3), more preferably at least 90 vol. % of the lower boiling product stream from step (3), most preferably at least 95 vol. % of the lower boiling product stream from step (3), to the esterification reaction vessel of step (1); and, optionally (5) removing water from the higher boiling product stream of step (3).

A fourth aspect of the present invention provides the use a carbon oxide selected from carbon monoxide and carbon dioxide to increase the selectivity towards methanol in a process for the hydrogenation of methyl acetate to ethanol and methanol in a hydrogenation unit containing a copper-zinc oxide hydrogenation catalyst, wherein the hydrogenation feed composition comprises methyl acetate and water, together with hydrogen, and wherein the hydrogenation of the methyl acetate is performed in the vapour phase and the carbon oxide is added to the hydrogenation unit In the first aspect of the present invention, a hydrogenation feed composition comprising methyl acetate and water, is fed together with hydrogen and at least one carbon oxide selected from carbon monoxide and carbon dioxide, into a hydrogenation unit containing a copper-zinc oxide hydrogenation catalyst and hydrogenating the methyl acetate to produce a hydrogenation product stream comprising ethanol, methanol, unreacted methyl acetate, water, unreacted hydrogen, carbon monoxide, carbon dioxide, and ethyl acetate, wherein said hydrogenation unit is operated in the vapour phase at elevated temperature and elevated pressure, and wherein the total molar ratio of hydrogen to methyl acetate fed to the hydrogenation unit is in the range of from 5:1 to 20:1, and the total molar ratio of methyl acetate to carbon oxide(s) fed to the hydrogenation unit is in the range of from 1:10 to 1000:1.

Preferably, the hydrogenation unit is operated at high conversion of methyl acetate to ethanol and methanol; in particularly, the hydrogenation unit is typically operated at an acetate ester conversion of at least 50 mol %, more preferably at least 80 mol %, even more preferably at least 85 mol %.

Whilst not wishing to be bound by theory, it is believed that the hydrogenation reaction occurring in the hydrogenation is an equilibrium reaction, with methyl acetate reacting with hydrogen to produce methanol and ethanol. Due to the presence of ethanol in the hydrogenation unit, and due to the equilibrium nature of the hydrogenation reaction, some ethyl acetate will be formed in the hydrogenation unit and will be present in the effluent stream from the hydrogenation unit.

It has been found that maintaining a concentration of water in the hydrogenation unit can be beneficial to the hydrogenation of methyl acetate over a copper-zinc oxide hydrogenation catalyst. In particular, the presence of water in the hydrogenation unit can provide benefits in terms of productivity and selectivity; additionally, concentrations of water may also limit the production of ethyl acetate through trans-esterification in the hydrogenation unit.

Whilst not wishing to be bound by theory, it is believed that the presence of water in the hydrogenation unit can disadvantageously lead to the promotion of methanol steam reforming over the hydrogenation catalyst and generate carbon dioxide through the process indicated below:

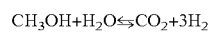

$$CH_3OH + H_2O \leftrightarrows CO_2 + 3H_2$$

Further, since the hydrogenation catalyst is also active for the water gas shift reaction, the carbon dioxide generated in the methanol steam reforming reaction can then subsequently be converted in the hydrogenation unit to carbon monoxide by the reverse water gas shift reaction through the process indicated below:

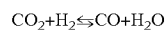

$$CO_2 + H_2 \leftrightarrows CO + H_2O$$

Thus, through methanol steam reforming and reverse water gas shift, the selectivity towards methanol in the hydrogenation unit is reduced (i.e. less methanol is present in the hydrogenation product stream than would be expected based on the amount of methyl acetate and other sources of methanol in the feed to the hydrogenation unit).

It has advantageously been observed that co-feeding at least one carbon oxide selected from carbon monoxide and carbon dioxide, to the hydrogenation unit improved the selectivity towards methanol compared to when no carbon oxide(s) is present without significantly inhibiting the hydrogenation reaction.

In the hydrogenation unit, the total molar ratio of hydrogen to methyl acetate in the hydrogenation unit is in the range of from 5:1 to 20:1, preferably in the range of from 5:1 to 18:1, more preferably in the range of from 5:1 to 15:1, such as from 8:1 to 12:1.

In the hydrogenation unit, the total molar ratio of methyl acetate to carbon oxide(s) fed to the hydrogenation unit is in the range of from 1:2 to 100:1, preferably from 1:1 to 50:1, more preferably from 2:1 to 20:1, most preferably from 2:1 to 10:1. As used herein, the reference to "carbon oxide(s)" is a reference to the single carbon oxide selected from carbon monoxide or carbon dioxide that is fed to the hydrogenation unit when only a single carbon oxide is fed to the hydrogenation unit, or the combination of both carbon monoxide and carbon dioxide when both carbon monoxide and carbon dioxide are fed to the hydrogenation unit.

In one specific embodiment of the present invention, the at least one carbon oxide selected from carbon monoxide and carbon dioxide is carbon monoxide.

In another specific embodiment of the present invention, the at least one carbon oxide selected from carbon monoxide and carbon dioxide is carbon dioxide.

In another specific embodiment of the present invention, the at least one carbon oxide selected from carbon monoxide and carbon dioxide is a mixture of carbon monoxide and carbon dioxide. In the embodiment wherein the at least one carbon oxide selected from carbon monoxide and carbon dioxide is a mixture of carbon monoxide and carbon dioxide, any ratio of carbon monoxide to carbon dioxide may be used, typically the ratio of carbon monoxide to carbon dioxide is in the range of from 100:1 to 1:100, more typically in the range of from 50:1 to 1:50, such as from 10:1 to 1:10, for example from 5:1 to 1:5 or from 2:1 to 1:2.

The hydrogen and the carbon oxide(s) that is fed to the hydrogenation unit may be fed in a single combined feed or in two or more separate feeds.

If the hydrogen and carbon oxide(s) are fed to the hydrogenation unit as a single feed, the ratio of hydrogen and carbon oxide(s) in the feed gas is typically in the range of from 2.5:1 to 2000:1.

If the hydrogen and carbon oxide(s) are fed to the hydrogenation unit as two or more separate feeds, the feeds may be selected from substantially pure hydrogen, substantially pure carbon monoxide, substantially pure carbon dioxide, mixtures of hydrogen and carbon monoxide, mixtures of hydrogen and carbon dioxide, mixtures of carbon monoxide and carbon dioxide, and mixtures of hydrogen, carbon monoxide and carbon dioxide. In one embodiment wherein the hydrogen and carbon oxide(s) are fed to the hydrogenation unit as two or more separate feeds, the hydrogen and carbon oxide(s) are fed to the hydrogenation unit as one feed of substantially pure hydrogen and a second feed selected from substantially pure carbon monoxide, substantially pure carbon dioxide and mixtures of carbon monoxide and carbon dioxide. In another embodiment wherein the hydrogen and carbon oxide(s) are fed to the hydrogenation unit as two or more separate feeds, the hydrogen and carbon oxide(s) are fed to the hydrogenation unit as a first feed of substantially pure hydrogen and a second feed comprising a mixture of hydrogen and at least one carbon oxide.

The hydrogenation unit may consist of a single reactor or may comprise two or more reactors; if the hydrogenation unit comprises two or more reactors, the reactors may be arranged in series, in parallel, or a combination thereof. The reactor or reactors of the hydrogenation unit may be adiabatic or reactors incorporating heat removal means.

In the embodiments wherein two or more reactors are used in series, heat exchangers and/or intercoolers and/or additional reactant and/or recycle of intermediates can be employed in between successive reactors to control the reaction temperature and/or optimise the process.

In one specific embodiment of the present invention, the hydrogenation unit comprises one or more reactors incorporating heat removal means, preferably one or more multitubular reactors.

In another specific embodiment of the present invention, the hydrogenation unit comprises one or more adiabatic reactors. In this embodiment of the present invention, the hydrogenation unit preferably comprises two or more adiabatic reactors connected in series, more preferably from 2 to 12 adiabatic reactors connected in series, even more preferably from 3 to 10 adiabatic reactors connected in series, most preferably from 4 to 8 adiabatic reactors connected in series. Preferably, the temperature rise in a single adiabatic reactor is no more than 50° C., more preferably in the range of from 5 to 50° C., and most preferably in the range of from 10 to 25° C. The adiabatic reactors in a series of adiabatic reactors may be operated at different temperatures depending on composition of the individual reactor feeds in order to optimise conversion of methyl acetate to methanol and ethanol.

In another specific embodiment of the present invention, the hydrogenation unit comprises two or more adiabatic reactors connected in series, wherein all of the hydrogen and the carbon oxide(s) is fed to the first adiabatic reactor and part of the hydrogenation feed composition is fed to the first adiabatic reactor and the remaining part(s) of the hydrogenation feed composition is fed to the inlet of the second and/or subsequent adiabatic reactor(s) together with the effluent of the previous adiabatic reactor in the hydrogenation unit.

In another specific embodiment of the present invention, the hydrogenation unit comprises two or more adiabatic reactors connected in series, wherein part of the hydrogen and the carbon oxide(s) is fed to the first adiabatic reactor with the remaining part(s) of the hydrogen and carbon oxide(s) being fed to the subsequent adiabatic reactor(s), and part of the hydrogenation feed composition is fed to the first adiabatic reactor and the remaining part(s) of the hydrogenation feed composition is fed to the inlet of the second and/or subsequent adiabatic reactor(s) together with the effluent of the previous adiabatic reactor in the hydrogenation unit.

In another specific embodiment of the present invention, the hydrogenation unit comprises two or more adiabatic reactors connected in series, wherein over 50 mol % of the hydrogen and over 50 mol % of the carbon oxide(s) is fed to the first adiabatic reactor with the remaining portion of the hydrogen and the carbon oxide(s) being fed to the subsequent adiabatic reactor(s), and part of the hydrogenation feed composition is fed to the first adiabatic reactor and the remaining part(s) of the hydrogenation feed composition is fed to the inlet of the second and/or subsequent adiabatic reactor(s) together with the effluent of the previous adiabatic reactor in the hydrogenation unit.

In another specific embodiment of the present invention, the hydrogenation unit comprises two or more adiabatic reactors connected in series, wherein all of the hydrogenation feed composition is fed to the first adiabatic reactor and part of the hydrogen and the carbon oxide(s) is fed to the first adiabatic reactor and the remaining part(s) of the hydrogen and the carbon oxide(s) is fed to the inlet of the second and/or subsequent adiabatic reactor(s) together with the effluent of the previous adiabatic reactor in the hydrogenation unit.

The hydrogenation unit of the process of the present invention contains a copper-zinc oxide hydrogenation catalyst. The copper-zinc oxide hydrogenation catalysts may comprise the copper in either the elemental form or in a form which may be reduced to the elemental form of copper upon catalyst activation, such as in the form of copper oxide. In one particular embodiment of the present invention, the copper-zinc oxide hydrogenation catalyst contains copper in the form of copper oxide, and wherein at least part of the copper oxide present is reduced to the elemental form of copper in the hydrogenation unit.

The copper-zinc oxide hydrogenation catalysts used in the process of the present invention may be a supported or unsupported copper-zinc oxide catalyst.

In one embodiment of the present invention, the copper-zinc oxide hydrogenation catalyst is a supported copper-zinc oxide catalyst. In the embodiment wherein the copper-zinc oxide hydrogenation catalyst is a supported copper-zinc oxide catalyst, the support material may be selected from on any suitable support known to those skilled in the art; non-limiting examples of such supports include refractory oxide materials, carbon, clays, and mixtures thereof; preferred support materials are support materials comprising refractory oxide materials, such as silica, alumina, zirconia and mixed oxides; in one specific embodiment, the support material is alumina.

In another embodiment of the present invention, the copper-zinc oxide hydrogenation catalyst is an unsupported copper-zinc oxide catalyst.

In a preferred embodiment of the present invention, the copper-zinc oxide hydrogenation catalyst is an unsupported copper-zinc oxide catalyst consisting essentially of copper, zinc and oxygen. By the term "consisting essentially of copper, zinc and oxygen", it is meant that the copper-zinc oxide hydrogenation catalyst does not contain any other metals or other elements which would be catalytically active or act as a promoter in the hydrogenation reaction such as the hydrogenation reaction of the process of the present invention. In particular, the copper-zinc oxide hydrogenation catalyst preferably consists of copper oxide (CuO) and zinc oxide (ZnO), and wherein at least part of the copper oxide is reduced to elemental copper upon activation.

Preferably, the hydrogenation catalyst comprises from 10 to 80 wt % copper oxide, more preferably from 15 to 60 wt % copper oxide, most preferably from 20 to 40 wt % copper oxide, based on the total weight of the catalyst.

Preferably, the hydrogenation catalyst comprises from 20 to 90 wt % zinc oxide, more preferably from 40 to 85 wt % zinc oxide, most preferably from 60 to 80 wt % zinc oxide, based on the total weight of the catalyst.

Typically, before being employed in the process of the present invention, the copper-zinc oxide hydrogenation catalyst is activated. Activation of the copper-zinc oxide catalysts is known in the art. Conveniently, activation of the copper-zinc oxide hydrogenation catalyst can be performed by heating of the catalyst in a reducing atmosphere, such as heating the catalyst, preferably to a temperature of at least 180° C., more preferably at least 190° C., most preferably at least 200° C. in a hydrogen containing atmosphere. The catalyst activation under hydrogen is an exothermic process and so the most convenient method of activation is dependent on scale and would be known to a person skilled in the art; for example, the copper-zinc oxide hydrogenation catalyst may be conveniently activated by first being exposed to a flowing hydrogen containing atmosphere, wherein the partial pressure of hydrogen would be adjusted depending upon several factors such as heat removal and would be known to a skilled person; typically lower partial pressures of hydrogen would be used when heat removal is less efficient, although ranges of partial pressures of hydrogen from less than 0.1 bara up to 100 bara may be used, typically however, lower partial pressures of hydrogen would be used in the activation of the catalyst, such as from 0.01 bara to 10 bara, more typically from 0.05 to 2 bara, such as from 0.1 bara to 1 bara. Due to the exothermic nature of the catalyst activation, care should be taken such that the temperature of the catalyst does not increase to a point which causes the activated catalyst to have a reduced performance in the process of the present invention, such as a decrease in the activity of the catalyst caused by sintering or the formation of alloys on or in the catalyst; typically the temperature of the catalyst bed during catalyst activation should be controlled such that the temperature of the catalyst does not exceed 240° C. In one option, the activation of the copper-zinc oxide hydrogenation catalyst may be performed in the hydrogenation unit under an atmosphere containing hydrogen and at least one carbon oxide, such as the hydrogen and carbon oxide(s) mixture used in the process of the present invention. In another option, the activation of the copper-zinc oxide hydrogenation catalyst may be performed in the hydrogenation unit under a hydrogen containing atmosphere, preferably a diluted hydrogen containing atmosphere, such as an atmosphere consisting of hydrogen in an inert gas, preferably an atmosphere consisting of hydrogen in nitrogen.

The hydrogenation unit is operated in the vapour phase, that is, the hydrogen, carbon oxide(s), methyl acetate, water, methanol, ethanol and ethyl acetate, in the hydrogenation unit are in the vapour phase in the section of the reactor(s) where the hydrogenation reaction is occurring.

The temperature at which the hydrogenation unit is operated is preferably in the range of from 180 to 270° C., more preferably in the range of from 190 to 260° C., even more preferably 200 to 260° C. The pressure at which the hydrogenation unit is operated is preferably in the range of from 20 to 100 bara, more preferably in the range of from 30 to 80 bara, even more preferably in the range of from 40 to 70 bara.

The hydrogenation unit can be operated in batch or semi continuous or continuous mode. Continuous mode of operation is the most preferred.

The GHSV (under SATP conditions) for continuous operation of the hydrogenation unit is preferably in the range of from 50 to 50,000 $h^{-1}$, more preferably in the range of from 1,000 to 30,000 $h^{-1}$, and most preferably in the range of from 2,000 to 9,000 $h^{-1}$.

The source of the hydrogen gas that is fed to the hydrogenation unit is not limited and any suitable source of hydrogen may be used.

The source of the carbon oxide(s) gas that is fed to the hydrogenation unit is not limited and any suitable source of carbon oxide(s) may be used.

The hydrogenation feed composition comprising methyl acetate and water used in the process of the present invention may comprise other additional components, examples of other components that may be present in the hydrogenation feed composition include methanol, ethanol, ethyl acetate, propyl acetate, propanol, butyl acetate, butanol and acetic acid. In one embodiment, the hydrogenation feed composition additionally comprises methanol. In another embodiment, the hydrogenation feed composition may additionally comprise methanol, ethanol and ethyl acetate.

In one particular embodiment, at least 80 wt. %, preferably at least 85 wt %, most preferably at least 90 wt %, of the hydrogenation feed composition consists of methyl acetate, methanol and water.

In another particular embodiment, at least 90 wt. %, preferably at least 95 wt %, most preferably at least 98 wt %, of the hydrogenation feed composition consists of methyl acetate, methanol, water, ethanol and ethyl acetate.

In a preferred embodiment, the amount of water the hydrogenation feed comprises is in the range of from 0.1 to 10 mol %, preferably from 0.5 to 7 mol %.

In a preferred embodiment, the amount of methyl acetate in the hydrogenation feed composition is at least 50 mol. %, more preferably in the range of from 50 to 99.5 mol %, even more preferably in the range of from 50 to 90 mol %, such as from 55 to 90 mol % or from 60 to 90 mol %.

In a preferred embodiment, the amount of ethanol the hydrogenation feed comprises is in the range of from 0 to 5 mol %, preferably in the range of from 0 to 4 mol %, more preferably in the range of from 0 to 3 mol %, typically in the range of from 0.1 to 2.5 mol %, such as in the range of from 0.2 to 2 mol %.

In a preferred embodiment, the amount of ethyl acetate the hydrogenation feed comprises is in the range of from 0 to 5 mol %, preferably in the range of from 0 to 4 mol %, more preferably in the range of from 0 to 3 mol %, typically in the range of from 0.1 to 2.5 mol %, such as in the range of from 0.2 to 2 mol %.

The hydrogenation feed composition is liquid under SATP. Therefore, because the hydrogenation unit is operated in the vapour phase it is necessary to vaporise the hydrogenation feed composition prior to feeding it to the hydrogenation unit. The means by which the vaporisation of the hydrogenation feed composition is performed is not limited and any suitable means known in the art may be used.

The process of the present invention produces a hydrogenation product stream comprising ethanol, methanol, unreacted methyl acetate, unreacted hydrogen, carbon monoxide, carbon dioxide, water and ethyl acetate.

The amount of ethyl acetate in the hydrogenation product stream is preferably less than 3 mol % based on the total amount of the liquid portion of the hydrogenation product stream, that is, the components in the hydrogenation product stream that are liquid under standard ambient temperature and pressure (25° C. and 1 bara) (herein also referred to as "SATP"); more preferably, the amount of ethyl acetate in the hydrogenation product stream is less than 2 mol % based on the total amount of the liquid portion of the hydrogenation product stream.

In the process of the present invention, the hydrogenation product stream is separated into a first liquid product stream comprising the majority of the ethanol, methanol, unreacted methyl acetate, water, and ethyl acetate, and a first gaseous product stream comprising the majority of the unreacted hydrogen, carbon monoxide, and carbon dioxide, and wherein at least a portion of the first gaseous product stream is recycled to the hydrogenation unit.

The method of separation of the hydrogenation product stream into a first liquid product stream and a first gaseous product stream is not limited and any suitable method known to a person skilled in the art may be used.

In one specific embodiment of the present invention, the hydrogenation product stream is separated into the first liquid product stream and the first gaseous product stream by first cooling the hydrogenation product stream to a temperature such that the majority of the methanol, ethanol, methyl acetate, ethyl acetate and water present in the hydrogenation product stream condense and subsequently separating the cooled hydrogenation product stream into the first liquid product stream and the first gaseous product stream.

In a preferred embodiment of the present invention, the hydrogenation product stream is separated into the first liquid product stream and the first gaseous product stream by first cooling the hydrogenation product stream to a temperature below 120° C., preferably to a temperature below 80° C., and a pressure which is no more than 10 bar lower than the pressure of the hydrogenation unit, preferably no more than 5 bar lower than the pressure of the hydrogenation unit, such that the majority of the methanol, ethanol, methyl acetate, ethyl acetate and water present in the hydrogenation product stream condense and subsequently separating the cooled hydrogenation product stream into the first liquid product stream and the first gaseous product stream. More preferably, the cooling step of the separation of the first liquid product stream and the first gaseous product stream is performed at a pressure which has a pressure differential from the pressure of the hydrogenation unit of less than 10 bar, especially less than 5 bar; even more preferably is performed at a pressure which is lower than the pressure of the hydrogenation unit and having a pressure differential from the pressure of the hydrogenation unit of less than 10 bar, especially having a pressure differential from the pressure of the hydrogenation unit of less than 5 bar.

By the term "the majority of the methanol, ethanol, methyl acetate, ethyl acetate and water present in the hydrogenation product stream condense", it is meant that at least 50 mol %, preferably at least 60 mol %, more preferably at least 70 mol %, even more preferably at least 80 mol %, of the methanol, ethanol, methyl acetate, ethyl acetate and water present in the hydrogenation product stream condense.

The separation of the cooled hydrogenation product stream into a first liquid product stream which comprises the majority of the methanol, ethanol, methyl acetate, ethyl acetate and water, and a first gaseous product stream which comprises the majority of the unreacted hydrogen, carbon monoxide and carbon dioxide may be performed by any suitable means known in the art. For example, the separation may be performed in a distillation column or in a flash separation unit. In a preferred embodiment, the separation is performed in a flash separation unit.

It would be understood by a person skilled in the art that although the first gaseous product stream would consist of a majority of unreacted hydrogen, carbon monoxide and carbon dioxide, minor amounts of all of the other components present in the hydrogenation product stream would also be present in the gaseous phase as well as any by-products, in particular normally gaseous by-products (i.e. gaseous under SATP), such as methane and/or ethane, that may have been produced in the hydrogenation unit. Likewise, it would be understood by a person skilled in the art that although the first liquid product stream would comprise a majority of ethanol, methanol, unreacted methyl acetate, water and ethyl acetate, minor amounts of all of the other components present in the hydrogenation product stream would also be present in the liquid phase as well as any by-products, including minor amounts of normally gaseous by-products, that may have been produced in the hydrogenation unit.

By the term "first liquid product stream comprising the majority of the ethanol, methanol, unreacted methyl acetate, water and ethyl acetate", it is meant at least 50 mol %, preferably at least 60 mol %, more preferably at least 70 mol %, even more preferably at least 80 mol %, most preferably at least 90 mol %, of the ethanol, methanol, unreacted methyl acetate, water and ethyl acetate present in the cooled hydrogenation product stream are separated into the first liquid product stream. By the term "first gaseous product stream comprising the majority of the unreacted hydrogen, carbon monoxide and carbon dioxide", it is meant at least 50 mol %, preferably at least 60 mol %, more preferably at least 70 mol %, even more preferably at least 80 mol %, most preferably at least 90 mol %, of each of the unreacted hydrogen, carbon monoxide and carbon dioxide present in the cooled hydrogenation product stream are separated into the first gaseous product stream.

In the process of the present invention, at least part of the first gaseous product stream is recycled to the hydrogenation unit. Preferably, at least 80 vol. % of the first gaseous product stream, more preferably at least 90 vol. % of the first gaseous product stream, most preferably at least 95 vol. % of the first gaseous product stream, is recycled to the hydrogenation unit.

In a specific embodiment of the present invention, all of the first gaseous product stream may be recycled to the hydrogenation unit; however, a small bleed stream may be withdrawn from the recycle stream to control and/or reduce the build-up of inert components in the hydrogenation unit.

In another specific embodiment of the present invention, at least 98 vol %, typically in the range of from 98 to 99.5 vol %, of the first gaseous product stream is recycled to the hydrogenation unit.

The process of the first aspect of the present invention may be operated batchwise or continuously, preferably continuously.

A second aspect of the present invention provides a process for the manufacture of ethanol from acetic acid and hydrogen, wherein said process comprises the following steps:

(A) reacting acetic acid together with methanol in an esterification reaction vessel to produce a hydrogenation feed composition comprising methyl acetate and water;

(B) feeding the hydrogenation feed composition from step (A), together with hydrogen and at least one carbon oxide selected from carbon monoxide and carbon dioxide, into a hydrogenation unit and hydrogenating the methyl acetate to methanol and ethanol in accordance with the first aspect of the present invention;

(C) separating a lower boiling product stream comprising methanol, methyl acetate and ethyl acetate, and a higher boiling product stream comprising ethanol and water from the first liquid product stream produced in the process of step (B); and, optionally (D) removing water from the higher boiling product stream of step (C).

In step (A) of the second aspect of the present invention, methanol and acetic acid are reacted in an esterification reaction vessel to produce an esterification reaction product composition comprising methyl acetate and water. Said esterification reaction product composition comprising methyl acetate and water is then used as at least part of the hydrogenation feed composition for the hydrogenation unit in step (B).

The catalyst used in the esterification step of step (A) of the second aspect of the present invention is not limited and any known suitable catalyst for the esterification reaction may be employed.

Known esterification catalysts include mineral acids, such as hydrochloric acid and sulphuric acid; organic acids, such as organic sulphonic acids (e.g. para-toluene sulphonic acid and alkyl sulphonic acids, such as methane sulphonic acid); tin-based catalysts, such as di-butyl tin oxide; and, solid esterification catalysts, such as acidic zeolites, supported heteropolyacids and ion-exchange resins.

In one particular embodiment of the second aspect of the present invention, the esterification catalyst is a homogeneous catalyst. In this embodiment, the esterification catalyst is preferably selected from sulphuric acid, and organic sulphonic acids; more preferably, the esterification catalyst is an organic sulphonic acid; most preferably, the esterification catalyst is selected from para-toluene sulphonic acid and methane sulphonic acid. In one specific embodiment, the esterification catalyst is methane sulphonic acid.

In one particular embodiment of the second invention, the esterification catalyst is selected from sulphuric acid and organic sulphonic acids, and the esterification catalyst is present in the esterification reaction vessel in an amount in the range of from 0.1 to 10 wt %, preferably from 0.5 to 8 wt %, more preferably from 1 to 6 wt %, most preferably from 2 to 5 wt %, based on the weight of esterification catalyst adjusted to the equivalent weight of methane sulphonic acid relative to the total weight of the reaction mixture.

In the embodiment wherein the esterification catalyst is methane sulphonic acid, the methane sulphonic acid esterification catalyst may suitably be present in the esterification reaction vessel in an amount in the range of from 0.1 to 10 wt %, preferably from 0.5 to 8 wt %, more preferably from 1 to 6 wt %, most preferably from 2 to 5 wt %, based on the total weight of the reaction mixture.

The reaction mixture present in the esterification reaction vessel may also optionally contain a suitable amount of corrosion inhibitor, preferably between 0.1 and 1 wt % based on the total weight of the reaction mixture, to reduce corrosion of the vessel. A preferred corrosion inhibitor that may be used is copper in the form of a salt which is soluble in the reaction mixture and would not adversely affect the esterification reaction, for example copper acetate.

The source of acetic acid that is fed to the esterification reaction vessel in the second aspect of the present invention is not limited and any suitable source of acetic acid may be used. Non-limiting examples of processes suitable for the preparation of acetic acid include methanol carbonylation, acetaldehyde oxidation, ethylene oxidation, oxidative fermentation, and anaerobic fermentation.

A particularly suitable source of acetic acid that may be fed to the esterification reaction vessel may be derived from the carbonylation of methanol and/or its reactive derivatives in the presence of a suitable catalyst. Processes for producing acetic acid by the Group VIII metal catalysed, hydrocarbyl halide co-catalysed carbonylation of alcohols and/or their reactive derivatives, in particular methanol and/or its reactive derivatives, are well-known in the art. Representative of such art employing rhodium as the Group VIII noble metal catalyst may be mentioned, for example, U.S. Pat. No. 3,772,380; GB-A-1468940; GB-A-1538783 and EP-A-0087070. Representative of such art using iridium as the Group VIII noble metal catalyst may be mentioned, for example, GB-A-1234121; U.S. Pat. No. 3,772,380; DE-A-1767150; EP-A-0616997; EP-A-0618184; EP-A-0618183; and EP-A-0657386. Optionally, the process for the production of ethanol may be integrated with such methanol carbonylation processes.

Thus, in the second aspect of the present invention, the acetic acid fed to the esterification reaction vessel may be prepared from a methanol stream, together with carbon monoxide, in a carbonylation reaction. The methanol used in such carbonylation reactions is preferably prepared by a methanol synthesis reaction from synthesis gas, however said methanol stream may also emanate from another suitable source, such as a bio-fermentation process and/or pyrolysis (e.g. wood pyrolysis). Processes for the synthesis of methanol from synthesis gas are well known in the art.

The methanol used in the second aspect of the present invention is not limited and any suitable source of methanol, or combination of sources of methanol may be used. Suitable sources of methanol that may be used include methanol prepared by a methanol synthesis reaction from synthesis gas, as well as methanol from other suitable source, such as a bio-fermentation process, pyrolysis (e.g. wood pyrolysis) and/or methanol containing streams obtained in the process of the second aspect of the present invention. Suitable processes for the synthesis of methanol from synthesis gas are well known in the art.

Conveniently, if the acetic acid which is fed to an esterification vessel in the second aspect of the present invention is obtained from the carbonylation of methanol, the methanol from the same source as used in the preparation of the acetic acid may be used as at least a portion of the methanol required in step (A) of the second aspect of the present invention.

Thus, in specific embodiments of the present invention, it is possible to derive some or all of the reactants in the process of the present invention from synthesis gas.

The esterification reaction vessel used in step (A) of the second aspect of the present invention is not limited and any known esterification reaction vessel may be employed.

In step (A) of the second aspect of the process of the present invention, the esterification reaction product composition comprising methyl acetate and water may be additionally processed before it is used as the hydrogenation feed composition. For instance, the esterification reaction product composition comprising methyl acetate and water may be treated to reduce the amount of water present therein to within a desired concentration range prior to it being used as the hydrogenation feed composition, and/or the esterification reaction product composition comprising methyl acetate and water may be treated to remove or reduce the concentration of any unreacted acetic acid prior to it being used as the hydrogenation feed composition.

In step (B) of the second aspect of the present invention, the hydrogenation feed composition from step (A) is fed to a hydrogenation unit, together with hydrogen and at least one carbon oxide selected from carbon monoxide and carbon dioxide, and the methyl acetate is hydrogenated to methanol and ethanol in accordance with the first aspect of the present invention. Namely, step (b) of the second aspect of the present invention comprises feeding the hydrogenation feed composition comprising methyl acetate and water from step (A), together with hydrogen and at least one carbon oxide selected from carbon monoxide and carbon dioxide, into a hydrogenation unit containing a copper-zinc oxide hydrogenation catalyst and hydrogenating the methyl acetate to produce a hydrogenation product stream comprising ethanol, methanol, unreacted methyl acetate, water, unreacted hydrogen, carbon monoxide, carbon dioxide, and ethyl acetate, wherein said hydrogenation unit is operated in the vapour phase at elevated temperature, preferably at a temperature in the range of from 180 to 270° C., and elevated pressure, preferably in the range of from 20 to 100 bara, and wherein the total molar ratio of hydrogen to methyl acetate fed to the hydrogenation unit is in the range of from 5:1 to 20:1, and the total molar ratio of methyl acetate to carbon oxide(s) fed to the hydrogenation unit is in the range of from 1:2 to 100:1, and wherein the hydrogenation product stream is separated into a first liquid product stream comprising the majority of the ethanol, methanol, unreacted methyl acetate, water, and ethyl acetate, and a first gaseous product stream comprising the majority of the unreacted hydrogen, carbon monoxide, and carbon dioxide, and wherein at least a portion of the first gaseous product stream is recycled to the hydrogenation unit.

In step (C) of the second aspect of the present invention, the first liquid product stream from step (B) is separated into a lower boiling product stream comprising methanol, methyl acetate and ethyl acetate, and a higher boiling product stream comprising ethanol, water.

In one particular embodiment of the second aspect of the present invention, the first liquid product stream is separated into a lower boiling product stream comprising methanol, methyl acetate and ethyl acetate, and a higher boiling product stream comprising ethanol, water, in a distillation column operated at a head pressure of at most 5 bara, preferably at most 3 bara.

The separation of a lower boiling product stream comprising methanol, methyl acetate and ethyl acetate, and a higher boiling product stream comprising ethanol, water, from the first liquid product stream in step (C) of the second aspect of the present invention is preferably performed such that the higher boiling product stream contains less than 1.0 mol % methanol and the lower boiling product stream contains less than 0.5 mol % ethanol.

In one specific embodiment of the second aspect of the present invention, the lower boiling product stream contains less than 0.5 mol % ethanol.

In another specific embodiment of the second aspect of the present invention, the higher boiling product stream contains less than 1.0 mol % methanol.

Optionally, in the second aspect of the process of the present invention, at least part of the lower boiling product stream comprising methanol, methyl acetate and ethyl acetate may be recycled to the esterification reaction vessel. In the embodiments of the second aspect of the present invention wherein at least part of the lower boiling product stream comprising methanol, methyl acetate and ethyl acetate is recycled to the esterification reaction vessel, preferably at least 80 vol. % of the lower boiling product stream, more preferably at least 90 vol. % of the lower boiling product stream, most preferably at least 95 vol. % of the lower boiling product stream, is recycled to the esterification reaction vessel.

Optionally, in the second aspect of the present invention, an additional water removal step, optional step (D), may be performed on the higher boiling product stream comprising ethanol and water in order to remove water from the ethanol product. Conveniently, by use of a process comprising the optional water removal step, ethanol streams suitable for use in gasoline or for use as a chemical feedstock or solvent, may be conveniently prepared in accordance with the second aspects of the present invention.

The process of the second aspect of the present invention may be operated batchwise or continuously, preferably continuously.

A third aspect of the present invention provides a process for the production of ethanol from acetic acid and hydrogen, said process comprising the following steps:

(1) in an esterification reaction vessel, reacting methanol with acetic acid at elevated temperature in the presence of an esterification catalyst and an entrainer, said entrainer being sparingly soluble in water and forms a minimum boiling point azeotrope therewith, to form an esterification product composition comprising entrainer, unreacted methanol, methyl acetate and water, and, in a distillation column, recovering from the esterification product composition an overhead product fraction comprising methyl acetate, methanol and water, and, from an intermediate point in the distillation column, removing a liquid sidestream fraction comprising water, methanol, entrainer and methyl acetate; wherein the molar ratio of acetic acid to methanol in the esterification reaction vessel is in the range of from 1:1.1 to 1:1.8, preferably in the range of from 1:1.2 to 1:1.6, and the distillation column is operated at a head pressure of at most 5 bara, preferably at most 3 bara, more preferably at most 2 bara, and wherein the amount of water present in the overhead product fraction comprising methyl acetate, methanol and water is in the range of from 0.5 to 5 mol %;

(2) feeding a hydrogenation feed composition consisting of at least part of the overhead product fraction from step (1), together with hydrogen and at least one carbon oxide selected from carbon monoxide and carbon dioxide, into a hydrogenation unit and hydrogenating the methyl acetate to methanol and ethanol in accordance with the first aspect of the present invention;

(3) separating a lower boiling product stream comprising methanol, methyl acetate and ethyl acetate, and a higher boiling product stream comprising ethanol, water, from the first liquid product stream from step (2) in a distillation column operated at a head pressure of at most 5 bara, preferably at most 3 bara;

(4) recycling at least part of the lower boiling product stream from step (3), preferably at least 80 vol. % of the lower boiling product stream from step (3), more preferably at least 90 vol. % of the lower boiling product stream from step (3), most preferably at least 95 vol. % of the lower boiling product stream from step (3), to the esterification reaction vessel of step (1); and, optionally (5) removing water from the higher boiling product stream of step (3).

In step (1) of the third aspect of the present invention, methanol and acetic acid are reacted together at elevated temperature in the presence of an esterification catalyst and an entrainer in an esterification reaction vessel to form an esterification product composition comprising entrainer, methyl acetate and water, and, in a distillation column, from the esterification product composition is recovered an overhead product fraction comprising methyl acetate, methanol and water, and, from an intermediate point in the distillation column, a liquid sidestream fraction comprising water, methanol, entrainer and methyl acetate is removed. The entrainer used in step (1) is an entrainer that is sparingly soluble in water and forms a minimum boiling point azeotrope with the water, methanol and methyl acetate. The molar ratio of acetic acid to methanol in the esterification reaction vessel of step (1) is in the range of from 1:1.1 to 1:1.8, preferably in the range of from 1:1.2 to 1:1.6. The distillation column of step (1) is operated at a head pressure of at most 5 bara, preferably at most 3 bara, more preferably at most 2 bara. The amount of water present in the overhead product fraction recovered in step (1) is in the range of from 0.5 to 5 mol %.

The entrainer may suitably be added to the esterification reaction vessel of step (1) of the third aspect of the present invention, or may be added to a suitable point in the distillation column of step (1).

In a preferred embodiment of the third aspect of the present invention, the methanol and acetic acid are continuously fed to the esterification reaction vessel containing entrainer, methanol, acetic acid and esterification catalyst to produce an esterification product composition comprising entrainer, unreacted methanol, methyl acetate and water; continuously distilling from the product in a distillation column an overhead product fraction comprising methyl acetate, methanol and water, and continuously removing from an intermediate point in the distillation column a liquid sidestream fraction comprising water, methanol, entrainer and methyl acetate; then, from the liquid sidestream fraction, continuously separating a fraction comprising the majority of the methanol, entrainer and methyl acetate, from the water and returning said separated fraction comprising the majority of the methanol, entrainer and methyl acetate to a point in the distillation column of step (1) which is lower than the sidestream removal point.

In the third aspect of the present invention, the esterification reaction vessel may be separate from the distillation column of step (1) or integrated therewith. Preferably, the esterification reaction vessel is a kettle at the base of the distillation column, which suitably may contain not less than 8 theoretical stages and preferably from 15 to 50 theoretical stages. Whenever the esterification reaction vessel is separate from the distillation column of step (1) of the third aspect of the present invention, it is preferred to recycle the residue from the base of the distillation column to the esterification reaction vessel.

In the third aspect of the present invention, the molar ratio of acetic acid to methanol in the esterification reaction vessel of step (1) has to be maintained within a suitable range to control the amount of water that is present in the overhead product fraction. Whilst not wishing to be bound by theory, the overhead fraction from the distillation column of step (1) of the third aspect of the present invention will consist of the lowest boiling fractions present in the distillation column, and will typically comprise an intermediate composition between the azeotropes of methyl acetate/water and methyl acetate/methanol. Increasing the methanol excess will increase the proportion of the overhead fraction that is made up of the methyl acetate/methanol azeotrope and therefore reduce the amount of water present in the overhead product fraction. Due to the presence of ethyl acetate in the lower boiling product stream of step (3) of the third aspect of the present invention, ethyl acetate would also be present in the esterification reaction vessel of step (1) through the recycling of step (4). The ethyl acetate present in the esterification reaction vessel of the third aspect of the present invention would also form an ethyl acetate/water azeotrope that would be present in the overhead product fraction. Due to the relatively greater amount of water present in the ethyl acetate/water azeotrope compared to the methyl acetate/water azeotrope, the amount of methanol required in the esterification reaction vessel of the third aspect of the present invention in order to maintain the optimal amount of water in the overhead product fraction would increase with increasing amounts of ethyl acetate in the lower boiling product stream of step (3).

The elevated temperature of the esterification reaction in step (1) of the third aspect of the present invention may vary over a moderately wide range, but must be sufficient, in the embodiment wherein the esterification reaction vessel is integral with the distillation column in step (1), to distil methyl acetate, methanol, water and entrainer out of the reaction mixture. Thus, at atmospheric pressure, suitable reaction temperatures are in the range of from 90 to 150° C., preferably from 95 to 125° C. To achieve the elevated temperature, the reaction vessel may be provided with, for example, steam coils, or other forms of heating.

In the third aspect of the present invention, to ensure an efficient separation of the overhead product fraction containing water within an optimal concentration, the head pressure of the distillation column of step (1) is at most 5 bara, preferably at most 3 bara, more preferably at most 2 bara.

Preferably, reflux is provided to the distillation column of step (1) of the third aspect of the present invention, by condensing at least a portion, preferably all, of an overhead fraction of the distillation column of step (1) in a condenser and returning a portion of the condensate to the distillation column of step (1) (primary reflux), the remainder of the overhead fraction (remaining condensate and optionally uncondensed overhead fraction) being the overhead product fraction. The primary reflux ratio may suitably be in the range of from 1:2 to 10:1, preferably from 1:1 to 10:1, more preferably from 1:1 to 5:1 (defined as the ratio of reflux flow rate to distillate flow rate).

Based on operating the distillation column of step (1) of the third aspect of the present invention at atmospheric pressure, the sidestream fraction is preferably removed from the distillation column of step (1) at a point in the column at which the column temperature is in the range of from 70 to 120° C., such as in the range of from 70 to 90° C.; depending upon the actual pressure under which the distillation column of step (1) is operating, the point at which the sidestream would be removed from the column may be at a higher or lower temperature range, suitable temperature ranges would be readily calculated by a person skilled in the art. In terms of theoretical stages, this point should be not less than 5 and preferably not less than 10 theoretical stages from the base of the distillation column. In addition to water, methanol, methyl acetate and entrainer, the liquid sidestream fraction may optionally also contain ethyl acetate.

From the liquid sidestream fraction of the third aspect of the present invention, a fraction comprising the majority of the methanol, entrainer and methyl acetate, may suitably be separated from a fraction comprising the majority of the water. By the term "fraction comprising the majority of the methanol, entrainer and methyl acetate", it is meant that said fraction comprises at least 50 mol %, preferably at least 60 mol %, more preferably at least 70 mol %, of the total amount of methanol, entrainer and methyl acetate in the liquid sidestream fraction that is separated. By the term "fraction comprising the majority of the water", it is meant that said fraction comprises at least 50 mol %, preferably at least 60 mol %, more preferably at least 70 mol %, of the total amount of water in the liquid sidestream fraction that is separated. The separation of a fraction comprising the majority of the methanol, entrainer and methyl acetate from a fraction comprising the majority of the water may suitably be performed by decantation, wherein the fraction comprising the majority of the methanol, entrainer and methyl acetate forms an upper organic phase and is separated from a lower aqueous phase comprising the fraction comprising the majority of the water. Preferably, the separation of a fraction comprising the majority of the methanol, entrainer and methyl acetate from a fraction comprising the majority of the water may suitably be performed by optionally cooling the liquid sidestream such that it separates more effectively into an organic phase which consists of the fraction comprising the majority of the methanol, entrainer and methyl acetate and an aqueous phase which consists of the fraction comprising the majority of the water, and the organic phase and aqueous phase being separated by decantation. The fraction comprising the majority of the methanol, entrainer and methyl acetate is preferably returned to the esterification reaction vessel of the third aspect of the present invention or another suitable point in the esterification system of the third aspect of the present invention, such as the distillation column of step (1) or by being mixed with the lower boiling product stream recycled in step (4), more preferably it is returned to a point in the distillation column of step (1) which is lower than the sidestream fraction removal point. The fraction comprising the majority of the water may be disposed of, or may optionally be subjected to further steps to recover any methanol, entrainer, methyl acetate and optionally ethyl acetate present therein; optionally, said recovered methanol, entrainer, methyl acetate and optionally ethyl acetate may be returned to the esterification reaction vessel of the third aspect of the present invention or another suitable point in the esterification system, such as the distillation column of step (1) or by being mixed with the lower boiling product stream recycled in step (4). If the fraction comprising the majority of the water is subjected to further steps to recover any methanol, entrainer, methyl acetate and optionally ethyl acetate present therein, at least a portion of the remaining water from said fraction is disposed of in a suitable manner, optionally a portion of said water may be returned back to the decanter.

In the embodiment of the third aspect of the present invention wherein a fraction comprising the majority of the methanol, entrainer and methyl acetate is separated from the liquid sidestream fraction by decantation, the molar ratio of acetic acid to methanol in the esterification reaction vessel has to be maintained within a suitable range to ensure that the sufficient phase split occurs.

Increasing the methanol to acetic acid ratio in the esterification reaction vessel of the third aspect of the present invention, for instance to control the amount of water present in the overhead product fraction, will result in an increasing amount of methanol present in the vicinity of the distillation column at which the liquid sidestream is removed, this increasing amount of methanol may result in a weakening in the liquid phase separation in the liquid sidestream so that the water may not be as effectively removed from the esterification reaction vessel. In instances wherein the liquid phase separation in the liquid sidestream occurs, additional entrainer and/or water may be added to the liquid sidestream to provide a greater degree of liquid phase separation.

The distillation column in step (1) of the third aspect of the present invention may suitably incorporate means for facilitating the removal of a liquid sidestream fraction, said means may take the form of a deep weir or chimney tray located immediately below the point in the distillation column of step (1) from which the sidestream fraction is removed. Using such means it may be possible to maximise the concentration of water in the sidestream fraction by facilitating phase separation within the column.

To replace any entrainer lost overhead or in a fraction comprising the majority of the water, additional entrainer may be fed to the esterification reaction vessel of the third aspect of the present invention.

The entrainer may be any hydrocarbon, ether, ester, ketone, or mixture thereof, which is sparingly soluble in water and which forms a minimum boiling point azeotrope with water. Examples of suitable entrainers are toluene, diisobutyl ether, butyl acetate (n-butyl acetate, iso-butyl acetate, or mixtures thereof) and methyl isobutyl ketone. Thus, in one embodiment of the third aspect of the present invention, the entrainer is selected from toluene, diisobutyl ether, n-butyl acetate, iso-butyl acetate, methyl ethyl ketone, and mixtures thereof. Preferably, the entrainer is an acetic acid ester, such as n-butyl acetate. In the embodiment wherein the entrainer is an acetic acid ester, the entrainer may added to the esterification reaction vessel and/or the distillation column of step 1 as the acetic acid ester, or, alternatively, the ester may be formed in situ by adding the component alcohol, such as n-butanol when n-butyl acetate is used as the entrainer, to the esterification reaction vessel. Preferably, the entrainer is selected from a butyl acetate, more preferably n-butyl acetate.

The amount of entrainer present in the esterification reaction vessel may suitably be greater than 1 wt %, preferably from 1 to 25 wt %, based on the total contents of the esterification reaction vessel.

The esterification catalyst may be any known esterification catalyst which is suitable for use in the esterification of acetic acid with methanol such as those detailed in relation to the second aspect of the present invention.

The reaction mixture in the esterification vessel may also optionally contain a suitable amount of corrosion inhibitor, preferably between 0.1 and 1 wt % based on the total weight of the reaction mixture, to reduce corrosion of the vessel. A preferred corrosion inhibitor that may be used is copper in the form of a salt which is soluble in the reaction mixture and would not adversely affect the esterification reaction, for example copper acetate.

The source of acetic acid that is fed to the esterification reaction vessel of step (1) of the third aspect of the present invention is not limited and any suitable source of acetic acid may be used. Suitable sources of acetic acid that may be used in the third aspect of the present invention include those detailed in relation to the second aspect of the present invention.

The majority of the methanol that is fed to the esterification reaction vessel of step (1) of the third aspect of the present invention is from the recycle of the lower boiling product stream from step (4), preferably at least 80 mol %, more preferably at least 85 mol %, even more preferably at least 90 mol %, most preferably at least 95 mol %, of the methanol that is fed to the esterification reaction vessel of step (1) is from the recycle of the lower boiling product stream from step (4). Additional methanol may be added to the esterification reaction vessel of step (1) in order to maintain the desired molar ratio of acetic acid to methanol in the esterification reaction vessel. The source of any additional methanol that may be added to the esterification reaction vessel is not limited and any suitable source of methanol may be used. Examples of suitable sources of acetic acid, as well as their processes of preparation are provided above in relation to the second aspect of the present invention and are hereby incorporated by reference into the third aspect of the present invention.

It would be understood by the skilled person that during the initial start-up of the process of the third aspect of the present invention, a recycle stream of the lower boiling product stream would not be able to provide the original charge of methanol. Thus, the source of the original charge of methanol in the esterification reaction vessel of the third aspect of the present invention is not limited and any suitable source of methanol may be used. Preferably, methanol from the same source may be used as the original charge of methanol and as any additional methanol that may be added to the esterification reaction vessel.

Conveniently, if the acetic acid which is fed to an esterification vessel in the third aspect of the present invention is obtained from the carbonylation of methanol, the methanol from the same source as used in the preparation of the acetic acid may be used as the original charge of methanol and/or as any additional methanol which may be required during the process.

The process of the third aspect of the present invention results in very low levels of ethyl acetate being fed to the esterification reaction vessel through the recycle stream of step (4) due to the high conversion of methyl acetate to methanol and ethanol in the hydrogenation unit of step 2 and the separation of step (3). Advantageously, because very low levels of ethyl acetate are present in the esterification reaction vessel of step (1), the amount of water present in the overhead product fraction can be controlled to be within the desired range without the need to add methanol in amounts exceeding the acetic acid to methanol ratio of 1:1.8; advantageously, this enables the liquid sidestream fraction withdrawn from an intermediate point in the distillation column of step (1) to be more easily separated into an aqueous stream and an organic stream which may be recycled.

Through the use of the esterification system as described in step (1) of the third aspect of the process of the present invention, the overhead product fraction comprising methyl acetate, methanol and water comprises from 0.5 to 5 mol % water. It has been found that maintaining the water concentration in such a range is beneficial to the hydrogenation of methyl acetate over a copper-zinc oxide hydrogenation catalyst. In particular, a concentration of water in the specified range can provide benefits in terms of productivity and selectivity; additionally, concentrations of water in the specified range may also limit the production of ethyl acetate through trans-esterification in the hydrogenation unit and subsequently reduce the amount of ethyl acetate that may be recycled to the esterification reaction vessel.

In a particularly preferred embodiment of the process of the third aspect of the present invention, all of the overhead product fraction comprising methyl acetate, methanol and water from step (1), is passed directly to a means for vaporising said fraction and said vaporised overhead product fraction comprising methyl acetate, methanol and water is fed directly from the vaporising means to the hydrogenation unit as the hydrogenation feed composition.

In the third aspect of the present invention, the first liquid product stream is separated into a lower boiling product stream comprising methanol, methyl acetate and ethyl acetate, and a higher boiling product stream comprising ethanol, water, in a distillation column operated at a head pressure of at most 5 bara, preferably at most 3 bara.

The separation of a lower boiling product stream comprising methanol, methyl acetate and ethyl acetate, and a higher boiling product stream comprising ethanol, water, from the first liquid product stream in the third aspect of the present invention is preferably performed such that the higher boiling product stream contains less than 1.0 mol % methanol and the lower boiling product stream contains less than 0.5 mol % ethanol.

In one specific embodiment of the third aspect of the present invention, the lower boiling product stream contains less than 0.5 mol % ethanol.

In another specific embodiment of the third aspect of the present invention, the higher boiling product stream contains less than 1.0 mol % methanol.

In the third aspect of the present invention, at least part of the lower boiling product stream, preferably at least 80 vol. % of the lower boiling product stream, more preferably at least 90 vol. % of the lower boiling product stream, most preferably at least 95 vol. % of the lower boiling product stream, is recycled to the esterification reaction vessel.

In the third aspect of the present invention, all of the lower boiling product stream may be recycled to the esterification reaction vessel; however, a small bleed stream may be withdrawn from the recycle stream to control the amount of ethyl acetate and/or ethanol being introduced to the esterification reaction vessel.

Optionally, in the third aspect of the present invention, an additional water removal step may be performed on the higher boiling product stream comprising ethanol and water in order to remove water from the ethanol product. Conveniently, by use of a process comprising the optional water removal step, ethanol streams suitable for use in gasoline or for use as a chemical feedstock or solvent, may be conveniently prepared in accordance with the third aspect of the present invention.

The process of the third aspect of the present invention may be operated batchwise or continuously, preferably continuously.

The processes of the second and/or the third aspects of the present invention can also be used to provide a process for the production of ethanol from methanol, carbon monoxide, hydrogen and optionally carbon dioxide, said process comprising the following steps:
(a) reacting methanol together with carbon monoxide in the presence of a suitable methanol carbonylation catalyst system to produce acetic acid;
(b) proceeding with a process according to the second or the third aspects of the present invention, wherein acetic acid used in the process is the acetic acid produced in step (a) above.

Preferably, in the embodiments of the second and/or third aspects of the present invention which provide a process for the production of ethanol from methanol, carbon monoxide, hydrogen and optionally carbon dioxide, the methanol used in the esterification step of the process is obtained from the same source as the methanol used in step (a) above.

Preferably, in the embodiments of the second or third aspects of the present invention which provide a process for the production of ethanol from methanol, carbon monoxide, hydrogen and optionally carbon dioxide, the methanol used in the esterification step of the process is obtained from synthesis gas by a methanol synthesis reaction. More preferably, in this embodiment, the hydrogen and the carbon oxide(s) which are fed to the hydrogenation unit and the carbon monoxide used for the carbonylation of methanol are obtained by separation of synthesis gas obtained from the same source as that used for the methanol synthesis reaction.

A fourth aspect of the present invention provides the use a carbon oxide selected from carbon monoxide and carbon dioxide to increase the selectivity towards methanol in a process for the hydrogenation of methyl acetate to ethanol and methanol in a hydrogenation unit containing a copper-zinc oxide hydrogenation catalyst, wherein the hydrogenation feed composition comprises methyl acetate and water, together with hydrogen, and wherein the hydrogenation of the methyl acetate is performed in the vapour phase and the carbon oxide is added to the hydrogenation unit. The preferred ranges and aspects of the process for the hydrogenation of methyl acetate to ethanol and methanol of the fourth aspect of the present invention include those ranges and processes as detailed in relation to any of the first, second and third aspects of the present invention.

EXAMPLES

Examples 1 to 5 and Comparative Examples A and B

Two copper-zinc oxide catalysts were used in Examples 1 to 5 and Comparative Examples A and B: Pricat CZ 29/2T (Trade Mark) (supplied by Johnson Matthey), 35 wt. % CuO, 65 wt. % ZnO; T-2130 (supplied by Süd-Chemie), 33 wt. % CuO, 67 wt. % ZnO. Both catalysts were received in pellet form and were crushed and sieved before testing. The 300-500 µm sieve fraction was used in Examples 1 to 5 and Comparative Examples A and B.

Catalyst Testing

Catalyst testing was carried out in parallel high pressure fixed bed reactors. Two reactors were loaded with Pricat CZ 29/2T and one with T-2130. 1.5 g (approx. 1 mL) of catalyst was used in each reactor. The catalysts were heated to 100° C. under a flow of nitrogen at 2.5 MPa and a GHSV of 1500 $h^{-1}$. Hydrogen was then introduced into the nitrogen flow and the concentration of hydrogen was increased in stages to 20, 40 and then 70 vol % with a 0.5 hour dwell time at each stage. The hydrogen concentration was then raised to 100 vol % and the GHSV increased to 6000 $h^{-1}$. After 0.5 hour the temperature was ramped at a rate of 1° C./min to 200° C. where the conditions were held for a dwell time of 1.5 hours. At this point catalyst activation was considered complete.

In each of Examples 1 to 5, mixtures of hydrogen, carbon monoxide, methyl acetate, methanol and water were passed over the Pricat CZ 29/2T and T-2130 catalysts. n-Heptane was used at low concentration as an inert internal standard. In Comparative Examples A and B, the catalysts were tested in the absence of carbon monoxide. The reaction products were detected and quantified by gas chromatography.

The feed compositions and conditions used for each of the examples and comparative examples are provided in Table 1. Each Experiment lasted at least 24 hours. The experimental results from the examples and comparative examples are provided in Table 2. The values presented for ester conversion and methanol selectivity are representative results calculated by averaging at least four separate data points.

| E.g. | Temp. (° C.) | Pres. (barg) | GHSV ($h^{-1}$) | $H_2$ (vol %) | CO (vol %) | MeOAc (vol %) | MeOH (vol %) | $H_2O$ (vol %) | $n\text{-}C_7H_{16}$ (vol %) | $H_2$:MeOAc molar ratio | MeOAc:CO molar ratio |
|---|---|---|---|---|---|---|---|---|---|---|---|
| A | 210 | 50 | 4500 | 88.13 | 0.00 | 8.81 | 2.35 | 0.59 | 0.12 | 10 | N/A |
| 1 | 210 | 50 | 4500 | 87.25 | 0.88 | 8.81 | 2.35 | 0.59 | 0.12 | 10 | 10 |
| 2 | 210 | 50 | 4500 | 86.37 | 1.76 | 8.81 | 2.35 | 0.59 | 0.12 | 10 | 5 |
| 3 | 210 | 50 | 4500 | 83.73 | 4.41 | 8.81 | 2.35 | 0.59 | 0.12 | 10 | 2 |
| B | 240 | 50 | 12000 | 88.13 | 0.00 | 8.81 | 2.35 | 0.59 | 0.12 | 10 | N/A |
| 4 | 240 | 50 | 12000 | 87.25 | 0.88 | 8.81 | 2.35 | 0.59 | 0.12 | 10 | 10 |
| 5 | 240 | 50 | 12000 | 86.37 | 1.76 | 8.81 | 2.35 | 0.59 | 0.12 | 10 | 5 |

TABLE 2

| Catalyst | Example | Temp (° C.) | MeOAc:CO molar ratio | Methanol Selectivity (%) | Ester Conversion (%) |
|---|---|---|---|---|---|
| Pricat CZ 29/2T | Comparative A | 210 | N/A | 96.0 | 88.1 |
| | 1 | 210 | 10 | 98.5 | 84.2 |
| | 2 | 210 | 5 | 98.5 | 84.4 |
| | 3 | 210 | 2 | 104.0 | 85.0 |
| | Comparative B | 240 | N/A | 91.4 | 94.9 |
| | 4 | 240 | 10 | 93.7 | 93.5 |
| | 5 | 240 | 5 | 95.7 | 92.6 |
| Pricat CZ 29/2T (repeat) | Comparative A | 210 | N/A | 96.0 | 87.3 |
| | 1 | 210 | 10 | 98.1 | 83.6 |
| | 2 | 210 | 5 | 98.3 | 83.6 |
| | 3 | 210 | 2 | 103.7 | 83.9 |
| | Comparative B | 240 | N/A | 91.1 | 94.8 |
| | 4 | 240 | 10 | 93.4 | 93.3 |
| | 5 | 240 | 5 | 95.6 | 92.5 |

TABLE 2-continued

| Catalyst | Example | Temp (° C.) | MeOAc:CO molar ratio | Methanol Selectivity (%) | Ester Conversion (%) |
|---|---|---|---|---|---|
| T-2130 | Comparative A | 210 | N/A | 96.5 | 79.2 |
| | 1 | 210 | 10 | 98.6 | 77.5 |
| | 2 | 210 | 5 | 98.4 | 79.0 |
| | 3 | 210 | 2 | 104.2 | 79.8 |
| | Comparative B | 240 | N/A | 92.1 | 92.6 |
| | 4 | 240 | 10 | 94.1 | 89.8 |
| | 5 | 240 | 5 | 96.0 | 88.8 |

The results presented for Examples 1, 2 and 3 and Comparative Example A, which were conducted at 210° C., and Examples 4 and 5 and Comparative Example B, which were all conducted at 240° C., demonstrate that the methanol selectivity was higher when carbon monoxide was present compared to when it was not.

Examples 6 to 9 and Comparative Examples C to E

Catalyst Testing

Catalyst testing was carried out in parallel pressure flow reactors. 1.5 g (approx. 1 mL) of catalyst was used in each reactor. The catalysts were heated to 100° C. under a flow of 5 mol % $H_2$ in $N_2$ at 2.5 MPa and a GHSV of 6000 $h^{-1}$. The concentration of $H_2$ was increased in stages to 10, 20, 40, 70 and 100 mol % with a 1 hour dwell time at each stage. The catalysts were then heated at a rate of 1° C./min to a holding temperature of 200° C. where the conditions were held for a dwell time of 1.5 hours. At this point catalyst activation was considered complete.

In Comparative Examples C and D and Examples 6 and 7, Pricat CZ 29/2T was tested. In Comparative Example E and Examples 8 and 9, Pricat CZ 29/2T and T-2130 were tested in separate reactors. Both catalysts were received in pellet form and were crushed and sieved before testing. The 300-500 μm sieve fraction was used.

In Comparative Examples C and D a mixture of $H_2$, methyl acetate and water was used. In Examples 6 and 7, a mixture of $H_2$, CO, $CO_2$, methyl acetate and water was used and in Examples 8 and 9 a mixture $H_2$, CO, $CO_2$, methyl acetate, water and methanol was used. Comparative Example E was performed in the same manner as Example 8, except that nitrogen gas substituted for the CO and $CO_2$. n-Heptane was used at low concentration as an inert internal standard in all experiments. The reaction products were detected and quantified by gas chromatography.

The feeds and conditions used for each experiment are given in Table 3. The experimental results are presented in Table 4. The values presented for ester conversion and methanol selectivity are representative results calculated by averaging at least four separate data points.

TABLE 4

| Catalyst | Example | Temp. (° C.) | MeOAc to carbon oxides molar ratio | Methanol selectivity (%) | Ester Conversion (%) |
|---|---|---|---|---|---|
| Pricat | C | 200 | N/A | 93.5 | 86.8 |
| CZ | D | 210 | N/A | 93.6 | 97.6 |
| 29/2T | 6 | 200 | 3.2 | 96.9 | 57.3 |
| | 7 | 210 | 3.2 | 97.6 | 84.5 |
| | 8 | 210 | 3.4 | 95.7 | 84.1 |
| | 9 | 215 | 3.4 | 95.3 | 92.9 |
| | E | 210 | N/A | 91.6 | 91.5 |
| T-2130 | 8 | 210 | 3.4 | 95.6 | 74.6 |
| | 9 | 215 | 3.4 | 95.3 | 86.0 |
| | E | 210 | N/A | 92.1 | 80.2 |

The results presented for Examples 6 to 9 and Comparative Examples C to E demonstrate that that methanol selectivity was greater when a mixture of carbon monoxide and carbon dioxide were present in the reactor feed. In Example 6, the ester conversion was significantly lower than in Comparative Example C; however, the ester conversion was increased by raising the temperature to 210° C. in Example 7. Despite this higher temperature, the methanol selectivity in Example 7, where carbon oxides were present in the hydrogenation feed, was higher than in Comparative Example C where they were not.

Examples 10 to 17

Reactor Description and Catalyst Loading

Catalyst testing was carried out in a high pressure fixed bed reactor. The internal diameter of the reactor was 24 mm and it was equipped with a centre-line thermowell with an outer diameter of 6.6 mm. The catalyst tested was Pricat CZ 29/2T™ (supplied by Johnson Matthey), 35 wt. % CuO, 65 wt. % ZnO. The catalyst was supplied as 5×4 mm (diameter×height) cylindrical pellets and was used as received. Pricat CZ 29/2T (160 g, approx. 100 mL) was loaded into the reactor. The catalyst bed length was approx. 350 mm; the reactor was operated in down-flow mode. The catalyst bed was heated externally by a jacket heater divided into two zones. The first zone (zone 1) heated the front quarter of the catalyst bed, the second zone (zone 2) heated the remaining three quarters of the bed.

A short distance after the outlet of the reactor was a condenser which was operated at the same pressure as the reactor but at lower temperature (40° C.). The level of the liquid phase in the condenser vessel was monitored; liquid was released via a control valve to maintain a constant liquid level. The vapour fraction from the condenser was passed to a compressor from which it was recycled to the reactor inlet. Gas could be purged from the recycle loop using an outlet located between the condenser and the recycle compressor. The purge flow rate could be set to any percentage of the

| E.g. | Temp (° C.) | Pres. (barg) | GHSV ($h^{-1}$) | $H_2$ (vol %) | CO (vol %) | $CO_2$ (vol %) | MeOAc (vol %) | MeOH (vol %) | $H_2O$ (vol %) | n-$C_7H_{16}$ (vol %) | $N_2$ (vol %) | $H_2$:MeOAc molar ratio | MeOAc to carbon oxides molar ratio |
|---|---|---|---|---|---|---|---|---|---|---|---|---|---|
| C | 200 | 50 | 5000 | 90.82 | 0 | 0 | 8.64 | 0 | 0.45 | 0.09 | 0 | 10 | N/A |
| D | 210 | 50 | 5000 | 90.82 | 0 | 0 | 8.64 | 0 | 0.45 | 0.09 | 0 | 10 | N/A |
| 6 | 200 | 50 | 5000 | 88.12 | 0.90 | 1.80 | 8.64 | 0 | 0.45 | 0.09 | 0 | 10 | 3.2 |
| 7 | 210 | 50 | 5000 | 88.12 | 0.90 | 1.80 | 8.64 | 0 | 0.45 | 0.09 | 0 | 10 | 3.2 |
| 8 | 210 | 50 | 5250 | 85.87 | 0.86 | 1.72 | 8.60 | 2.29 | 0.57 | 0.09 | 0 | 10 | 3.4 |
| 9 | 215 | 50 | 5250 | 85.87 | 0.86 | 1.72 | 8.60 | 2.29 | 0.57 | 0.09 | 0 | 10 | 3.4 |
| E | 210 | 50 | 5250 | 85.87 | 0 | 0 | 8.60 | 2.29 | 0.57 | 0.09 | 2.58 | 10 | N/A | recycle flow rate between 0% (i.e. operation in total recycle) and 100% (once-through mode). Ordinarily, the unit was run with a small bleed of between 0.5 and 2% of the recycle flow to manage the build-up of inerts (e.g. methane and ethane) but to maximize utilisation of hydrogen and retain methanol selectivity.

Before reaching the reactor, the recycle flow was mixed with a liquid feed (methyl acetate/methanol/water) and a fresh hydrogen make-up feed (high purity $H_2$: 99.995%). This mixture was passed to an evaporator (a small fixed bed reactor tube packed with inert material); the resulting vapour-phase reactant mixture was then passed into the reactor.

Catalyst Testing

In the above-described reactor, the catalyst was activated and the liquid feed was introduced to the reactor via the evaporator. The temperature of the condenser was set to 40° C. and the majority of the components liquid at room temperature (methyl acetate, methanol, ethanol, ethyl acetate and water) were drained continuously from the condenser vessel via a control valve with the liquid volume in the condenser being maintained at a constant level. A portion (but not the majority) of the CO and $CO_2$ left the system dissolved in the liquid product. The majority of the permanent gases including the $H_2$, CO and $CO_2$ remained in the recycle loop together with small concentrations of the normally liquid components. Inert gases, particularly methane and ethane, built-up in the recycle loop and low concentrations of acetaldehyde (<100 ppm) were also observed in the recycle loop as well as trace levels of other light organics. The concentration of inerts in the recycle was managed via a purge flow which was maintained at 1% or 0.5% of the recycle flow. The reactor pressure was maintained by dosing enough fresh $H_2$ to compensate for volume lost from the system.

The reactants were introduced to the reactor and the reaction was allowed to proceed until the gaseous components in the recycle loop had reached a steady state composition. The liquid feed used in Examples 10 to 17 had the following composition: methyl acetate 92.1 wt. %, methanol 6.5 wt. %, water 1.4 wt. %. The feed rates and reaction conditions used in Examples 10 to 17 are detailed in Table 5 below. The recycle flow rate was measured after the purge point

TABLE 5

| Example | Temperature (° C.) zone 1/zone 2 | Reactor Pressure (barg) | Liquid feed rate (g/h) | $H_2$ make-up (mol/h) | Recycle flow (mol/h) | Purge rate (% of recycle) | GHSV ($h^{-1}$) |
|---|---|---|---|---|---|---|---|
| 10 | 208/217 | 50 | 138.3 | 3.09 | 13.6 | 1.0 | 4670 |
| 11 | 209/218 | 50 | 138.4 | 3.09 | 13.6 | 1.0 | 4673 |
| 12 | 209/218 | 40 | 138.1 | 2.88 | 13.6 | 1.0 | 4603 |
| 13 | 209/218 | 40 | 138.5 | 3.00 | 17.1 | 0.8 | 5500 |
| 14 | 209/218 | 40 | 69.6 | 1.78 | 17.2 | 0.8 | 4959 |
| 15 | 209/218 | 40 | 173.5 | 3.27 | 17.0 | 0.8 | 5695 |
| 16 | 209/218 | 40 | 172.7 | 3.23 | 17.1 | 0.5 | 5690 |
| 17 | 229/238 | 40 | 173.2 | 3.59 | 17.0 | 0.5 | 5762 |

The concentrations of methyl acetate, ethyl acetate, methanol, ethanol, CO and $CO_2$ were measured by gas chromatograph at the outlet of the reactor and in the gas recycle loop. The concentrations measured at the reactor outlet (i.e. before the condenser) are given in Table 6. The concentrations measured in the recycle loop are given in Table 7. These results are averages over at least two data points collected once the gas compositions had reached steady state. The results of Examples 10 to 17 are presented in Table 8.

TABLE 6

| | Concentration in reactor outlet | | | | | |
|---|---|---|---|---|---|---|
| Example | MeOAc (vol %) | EtOAc (vol %) | MeOH (vol %) | EtOH (vol %) | CO (vol %) | $CO_2$ (vol %) |
| 10 | 1.14 | 0.40 | 10.70 | 8.22 | 0.76 | 1.14 |
| 11 | 1.08 | 0.39 | 10.75 | 8.30 | 0.79 | 1.17 |
| 12 | 1.59 | 0.52 | 10.45 | 7.75 | 1.26 | 1.77 |
| 13 | 1.14 | 0.38 | 8.97 | 6.75 | 1.03 | 1.21 |
| 14 | 0.12 | 0.05 | 5.50 | 4.45 | 0.49 | 0.35 |
| 15 | 2.32 | 0.62 | 9.94 | 7.00 | 1.18 | 1.71 |
| 16 | 2.35 | 0.63 | 9.88 | 6.94 | 1.22 | 1.69 |
| 17 | 1.15 | 0.47 | 10.83 | 8.37 | 4.89 | 4.43 |

TABLE 7

| | Concentration in recycle gas | | | | | | |
|---|---|---|---|---|---|---|---|
| Example | MeOAc (vol %) | EtOAc (vol %) | MeOH (vol %) | EtOH (vol %) | CO (vol %) | $CO_2$ (vol %) | $H_2$ (vol %) |
| 10 | 0.18 | 0.03 | 0.31 | 0.09 | 1.01 | 1.34 | 96.5 |
| 11 | 0.17 | 0.03 | 0.31 | 0.09 | 1.08 | 1.39 | 96.2 |
| 12 | 0.28 | 0.04 | 0.39 | 0.11 | 1.60 | 2.11 | 94.9 |
| 13 | 0.24 | 0.04 | 0.41 | 0.12 | 1.27 | 1.38 | 95.3 |
| 14 | 0.04 | 0.01 | 0.39 | 0.14 | 0.54 | 0.38 | 96.7 |
| 15 | 0.41 | 0.05 | 0.41 | 0.11 | 1.50 | 1.98 | 95.0 |
| 16 | 0.41 | 0.05 | 0.40 | 0.10 | 1.54 | 2.00 | 95.1 |
| 17 | 0.22 | 0.05 | 0.42 | 0.13 | 6.28 | 5.36 | 86.4 |

TABLE 8

| Example | $H_2$ to MeOAc molar ratio | MeOAc to carbon oxides molar ratio | Methanol selectivity (%) | Ester conversion (%) |
|---|---|---|---|---|
| 10 | 9.3 | 5.4 | 99.2 | 84.7 |
| 11 | 9.3 | 5.2 | 99.2 | 85.4 |
| 12 | 9.0 | 3.5 | 98.6 | 79.5 |
| 13 | 10.9 | 3.9 | 99.0 | 82.1 |
| 14 | 21.0 | 5.5 | 99.5 | 96.2 |

TABLE 8-continued

| Example | $H_2$ to MeOAc molar ratio | MeOAc to carbon oxides molar ratio | Methanol selectivity (%) | Ester conversion (%) |
|---|---|---|---|---|
| 15 | 8.7 | 3.8 | 98.6 | 71.8 |
| 16 | 8.8 | 3.7 | 98.7 | 71.4 |
| 17 | 8.3 | 1.1 | 97.8 | 84.2 |

Definition of Calculations

| | |
|---|---|
| Methanol selectivity (%) | $100 \times [\text{MeOH}_{out} - \text{MeOH}_{in}] / [\text{MeOAc}_{in} - \text{MeOAc}_{out}]$ |
| Ester Conversion (%) | $100 \times (1 - [\text{MeOAc}_{out} + \text{EtOAc}_{out}] / [\text{MeOAc}_{in} + \text{EtOAc}_{in}])$ |
| H$_2$ to MeOAc molar ratio | $\text{H}_{2in} / \text{MeOAc}_{in}$ |
| MeOAc to carbon oxides molar ratio | $\text{MeOAc}_{in} / [\text{CO}_{in} + \text{CO}_{2in}]$ |

Methanol selectivity and ester conversion are per pass. MeOH$_{in}$, MeOAc$_{in}$ and EtOAc$_{in}$ are the molar flow rates of methanol, methyl acetate and ethyl acetate respectively at the reactor inlet. This definition includes methyl acetate and methanol present in the liquid feed and uncondensed methanol, methyl acetate and ethyl acetate present in the recycle gas. MeOH$_{out}$, MeOAc$_{out}$ and EtOAc$_{out}$ are the molar flow rates of methanol, methyl acetate and ethyl acetate respectively at the reactor outlet. H$_{2in}$ is molar flow rate of hydrogen at the reactor inlet, i.e. the sum of the molar flow rates of the make-up hydrogen and the hydrogen in the recycle gas. CO$_{in}$ and CO$_{2in}$ are the molar flow rates of CO and CO$_2$ at the reactor inlet.

The invention claimed is:

1. A process for the hydrogenation of methyl acetate to methanol and ethanol comprising feeding a hydrogenation feed composition comprising methyl acetate and water, together with hydrogen and at least one carbon oxide selected from carbon monoxide and carbon dioxide, into a hydrogenation unit containing a copper-zinc oxide hydrogenation catalyst and hydrogenating the methyl acetate to produce a hydrogenation product stream comprising ethanol, methanol, unreacted methyl acetate, water, unreacted hydrogen, carbon monoxide, carbon dioxide, and ethyl acetate, wherein said hydrogenation unit is operated in the vapour phase at elevated temperature and elevated pressure, and wherein the total molar ratio of hydrogen to methyl acetate fed to the hydrogenation unit is in the range of from 5:1 to 20:1, and the total molar ratio of methyl acetate to carbon oxide(s) fed to the hydrogenation unit is in the range of from 1:2 to 100:1, and wherein the hydrogenation product stream is separated into a first liquid product stream comprising the majority of the ethanol, methanol, unreacted methyl acetate, water, and ethyl acetate, and a first gaseous product stream comprising the majority of the unreacted hydrogen, carbon monoxide, and carbon dioxide, and wherein at least a portion of the first gaseous product stream is recycled to the hydrogenation unit.

2. A process according to claim 1, wherein the total molar ratio of hydrogen to methyl acetate fed to the hydrogenation unit is in the range of from 5:1 to 18:1.

3. A process according to claim 1, wherein the carbon oxide is carbon monoxide.

4. A process according to claim 1, wherein the carbon oxide is carbon dioxide.

5. A process according to claim 1, wherein the carbon oxide is a combination of carbon monoxide and carbon dioxide.

6. A process according to claim 1, wherein the copper-zinc oxide hydrogenation catalyst is an unsupported copper-zinc oxide catalyst.

7. A process according to claim 1, wherein the copper-zinc oxide hydrogenation catalyst is supported on a suitable catalyst support material.

8. A process according to claim 1, wherein the hydrogenation feed composition comprises from 0.5 to 5 mol % water.

9. A process according to claim 1, wherein the hydrogenation feed composition additionally comprises methanol.

10. A process according to claim 9, wherein at least 80 wt. % of the hydrogenation feed composition consists of methyl acetate, methanol and water.

11. A process according to claim 1, wherein the hydrogenation product stream is separated into the first liquid product stream and the first gaseous product stream by first cooling the hydrogenation product stream to a temperature such that the majority of the methanol, ethanol, methyl acetate, ethyl acetate and water present in the hydrogenation product stream condense and subsequently separating the cooled hydrogenation product stream into the first liquid product stream and the first gaseous product stream.

12. A process according to claim 1, wherein at least 80 vol. % of the first gaseous product stream is recycled to the hydrogenation unit.

13. A process for the manufacture of ethanol from acetic acid and hydrogen, wherein said process comprises the following steps:
(A) reacting acetic acid together with methanol in an esterification reaction vessel to produce a hydrogenation feed composition comprising methyl acetate and water;
(B) feeding the hydrogenation feed composition from step (A), together with hydrogen and at least one carbon oxide selected from carbon monoxide and carbon dioxide, into a hydrogenation unit and hydrogenating the methyl acetate to methanol and ethanol in accordance with the process of claim 1;
(C) separating a lower boiling product stream comprising methanol, methyl acetate and ethyl acetate, and a higher boiling product stream comprising ethanol and water from the first liquid product stream produced in the process of step (B); and, optionally
(D) removing water from the higher boiling product stream of step (C).

14. A process for the production of ethanol from acetic acid and hydrogen, said process comprising the following steps:
(1) in an esterification reaction vessel, reacting methanol with acetic acid at elevated temperature in the presence of an esterification catalyst and an entrainer, said entrainer being sparingly soluble in water and forms a minimum boiling point azeotrope therewith, to form an esterification product composition comprising entrainer, unreacted methanol, methyl acetate and water, and, in a distillation column, recovering from the esterification product composition an overhead product fraction comprising methyl acetate, methanol and water, and, from an intermediate point in the distillation column, removing a liquid sidestream fraction comprising water, methanol, entrainer and methyl acetate; wherein the molar ratio of acetic acid to methanol in the esterification reaction vessel is in the range of from 1:1.1 to 1:1.8 and the distillation column is operated at a head pressure of at most 5 bara, and wherein the amount of water present in the overhead product fraction comprising methyl acetate, methanol and water is in the range of from 0.5 to 5 mol %;
(2) feeding a hydrogenation feed composition consisting of at least part of the overhead product fraction from step (1), together with hydrogen and at least one carbon oxide selected from carbon monoxide and carbon dioxide, into a hydrogenation unit and hydrogenating the methyl acetate to methanol and ethanol in accordance with the process of claim 1;

(3) separating a lower boiling product stream comprising methanol, methyl acetate and ethyl acetate, and a higher boiling product stream comprising ethanol, water, from the first liquid product stream from step (2) in a distillation column operated at a head pressure of at most 5 bara;

(4) recycling at least part of the lower boiling product stream from step (3) to the esterification reaction vessel of step (1); and, optionally (5) removing water from the higher boiling product stream of step (3).

* * * * *